(12) United States Patent
Kwak

(10) Patent No.: US 8,177,727 B2
(45) Date of Patent: May 15, 2012

(54) METHOD AND DEVICE FOR OBJECTIVE AUTOMATED AUDIOMETRY

(75) Inventor: Sangyeop Kwak, Seoul (KR)

(73) Assignees: Earlogic Korea Inc., Mapo-Gu, Seoul (KR); Sangyeop Kwak, Mapo-Gu, Seoul (KR)

( * ) Notice: Subject to any disclaimer, the term of this patent is extended or adjusted under 35 U.S.C. 154(b) by 494 days.

(21) Appl. No.: 12/442,344

(22) PCT Filed: Jul. 31, 2007

(86) PCT No.: PCT/KR2007/003661
§ 371 (c)(1),
(2), (4) Date: Mar. 20, 2009

(87) PCT Pub. No.: WO2008/035850
PCT Pub. Date: Mar. 27, 2008

(65) Prior Publication Data
US 2010/0076338 A1   Mar. 25, 2010

(30) Foreign Application Priority Data

Sep. 20, 2006   (KR) .................. 10-2006-0091469

(51) Int. Cl.
*A61B 5/00* (2006.01)
*A61B 5/04* (2006.01)
(52) U.S. Cl. ....................... 600/559; 600/544
(58) Field of Classification Search .......... 600/559, 600/544, 545, 558; 73/584, 585; 607/55
See application file for complete search history.

(56) References Cited

U.S. PATENT DOCUMENTS

| 4,649,482 | A | * | 3/1987 | Raviv et al. ............... 600/544 |
| 4,744,029 | A | * | 5/1988 | Raviv et al. ............... 600/544 |
| 6,602,202 | B2 | * | 8/2003 | John et al. ............... 600/559 |
| 7,014,613 | B2 | * | 3/2006 | John et al. ............... 600/559 |

OTHER PUBLICATIONS

Munro, Kevin J., et al., "Asymmetry in the auditory brainstem response following experience of monaural amplification," Auditory and Vestibular Systems, NeuroReport, vol. 18, No. 17, Nov. 19, 2007, pp. 1871-1874.
Lasky, Robert E., "Rate and adaptation effects on the auditory evoked brainstem response in human newborns and adults," Hearing Research 111, 1997, pp. 165-176.
Hecox, Kurt, et al., "Brainstem auditory evoked responses in man. I. Effect of stimulus rise-fall time and duration," J. Acoust. Soc. Am., vol. 60, No. 5, Nov. 1976, pp. 1187-1192.

* cited by examiner

*Primary Examiner* — Jeffrey G Hoekstra
(74) *Attorney, Agent, or Firm* — Edwards Wildman Palmer LLP; Kongsik Kim

(57) ABSTRACT

The present invention relates to a method for automation of objective hearing test based on the assessment of auditory evoked potential (AEP), for shortening of testing time, and for the minimization of inaccuracy and errors which may be resulted from the automation and time shortening. The method includes the steps for: as a preliminary test, presenting standard test stimulus to a subject; searching the wave V peak and SN10 peak; and as a main test, presenting test stimulus of each frequency, searching the minimal intensity and determining objective hearing threshold of each frequency.

10 Claims, 2 Drawing Sheets

[Fig. 1]
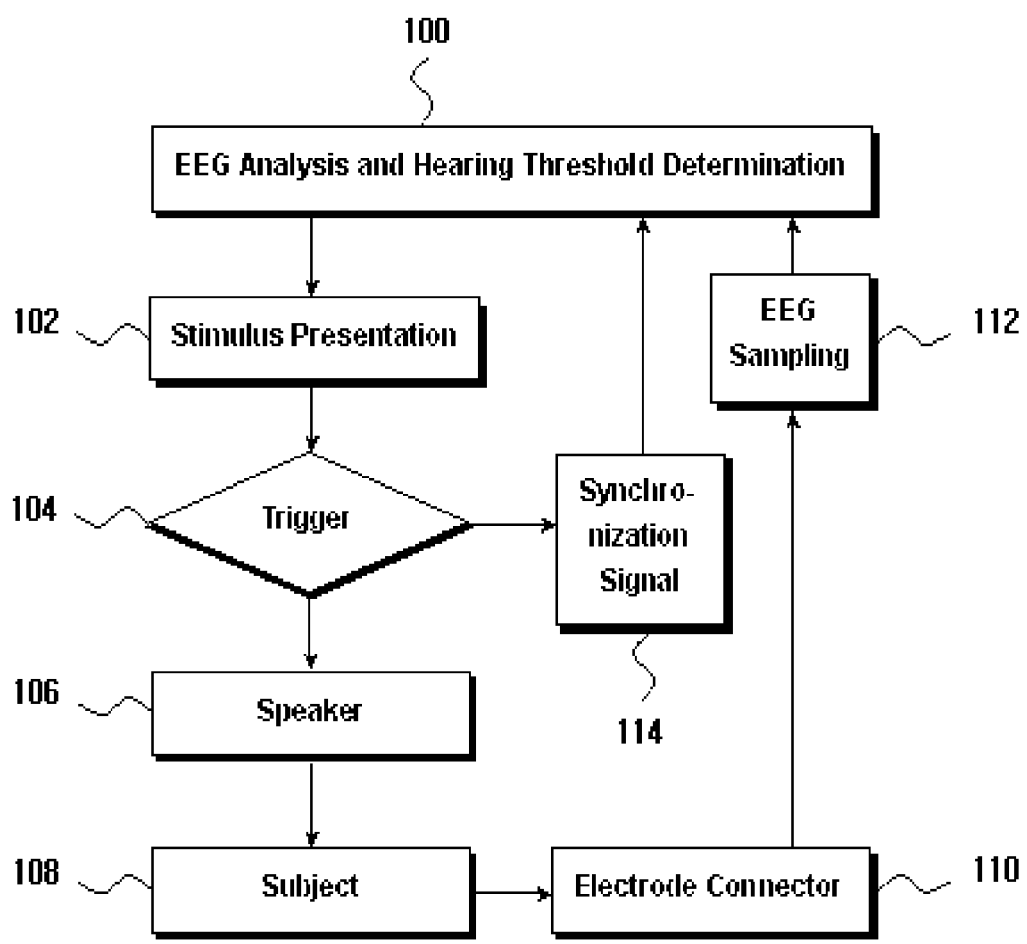

[Fig. 2]
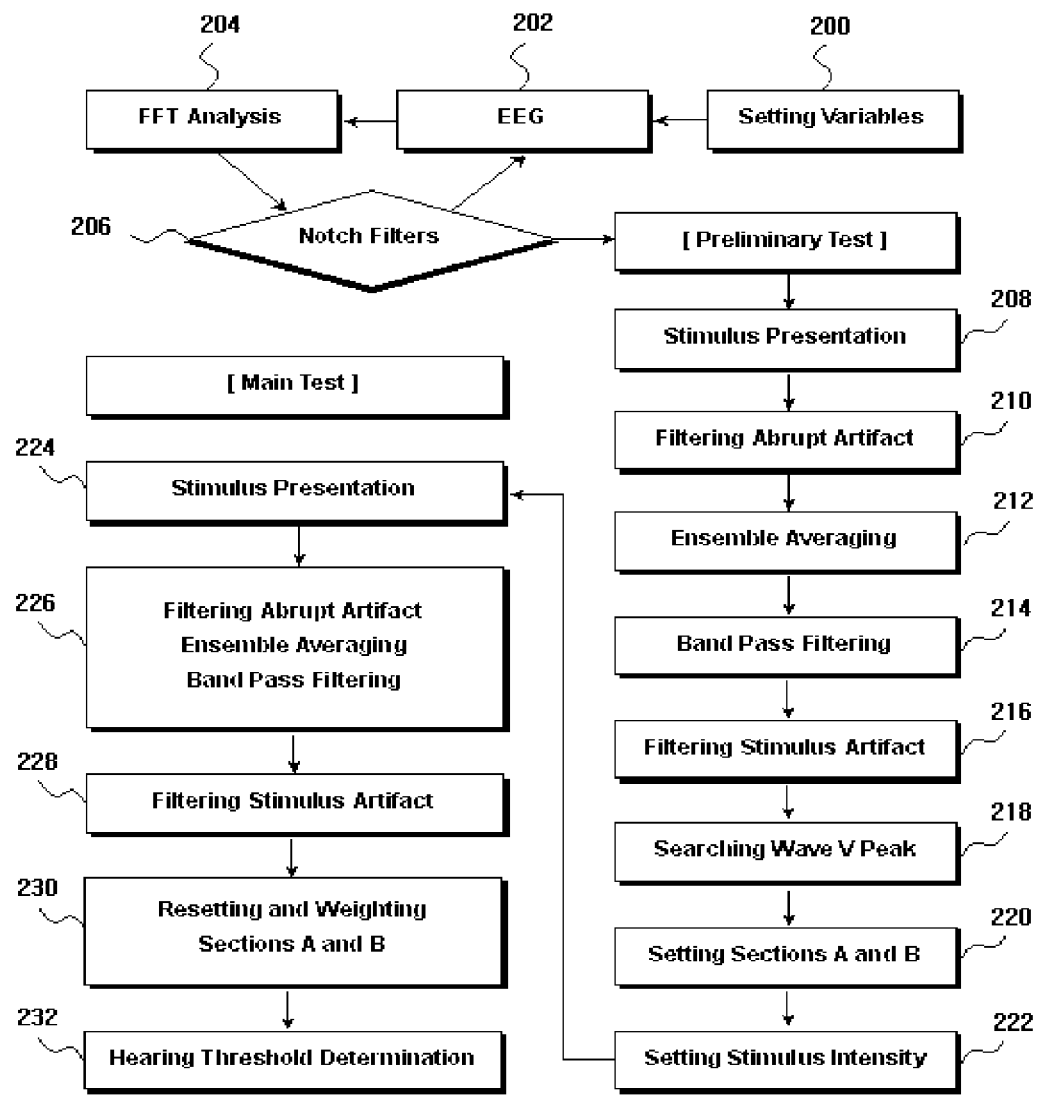

METHOD AND DEVICE FOR OBJECTIVE AUTOMATED AUDIOMETRY

TECHNICAL FIELD

The present invention relates to a method and device for automation of objective hearing test based on assessment of auditory evoked potential (AEP), for shortening testing time, and for minimization of inaccuracy and errors of hearing test that may be resulted from the automation and time shortening.

BACKGROUND ART

The auditory brainstem response (ABR) audiometry is the most widely used method for objective hearing test.

For ABR audiometry, an electrode is placed on a subject's head and test stimulus is repetitively presented at least more than 1,500 times. After averaging the data, patient's audibility is determined by presence or absence of Wave V.

Although a click is commonly used for ABR audiometry, this stimulus is inappropriate for estimate of hearing thresholds on specific frequencies, such as 250 Hz, 500 Hz, 1000 Hz, 2000 Hz, 4000 Hz, and 8000 Hz. For this reason, tone-pip (or tone-burst) stimulus which has very short duration and can be presented as individual frequency, is used for estimate of the frequency-specific threshold. In this case, the term "tone-pip (or tone-burst) ABR audiometry" is currently used.

DISCLOSURE OF INVENTION

In the conventional tone-pip ABR audiometry, as each frequency-specific threshold should be estimated separately, it takes about 1.5-2 hours to test hearing thresholds. In addition, because user's determination of a subject's hearing threshold depends on visual discrimination of wave V peak in which amplitude decrease more and more when stimulus intensity gets closer to hearing threshold, it is difficult to avoid intervention of user's subjective judgment.

It is the most serious problem of the conventional ton-pip ABR audiometry that very long time is required for the hearing test. It takes long time to set manually the test stimulus presented separately according to frequency and intensity. In addition, each test stimulus should be presented more than 1,500 times to obtain a significant signal-to-noise ratio. Most of all, because the more stimulus intensity gets closer to hearing threshold, the more amplitude of wave V decreases, it takes long time for a user to determine the presence or absence of wave V peak.

In order to solve above-mentioned problems of the conventional method, the present invention provides a method for automation of tone-pip (or tone-burst) ABR audiometry, which can exclude both manual operation and user's subjective judgment. Another object of the present invention is to provide a method for determining objective hearing threshold by computing the gap between wave V and SN10. Still another object of the present invention is to provide a method for obtaining excellent signal-to-noise ratio even after minimizing the number of averaging. Finally, the present invention provides a device for performing all above-mentioned objects.

In order to achieve above-mentioned objects, there is provided a method and device for objective automated hearing test comprising the steps of: (a) setting test condition which is arbitrarily done by a user before starting test; (b) converting subject's spontaneous EEG which is influxed from an electrode placed on a subject's head before starting test, into a real-time graphic image; (c) quantitative visualization of FFT analysis data on periodic artifacts among subject's spontaneous EEG; (d) filtering distinctive periodic artifacts based on the FFT analysis data which is arbitrarily done by a user; (e) as a preliminary test, presenting standard test stimulus (e.g. 2 KHz, 90 dBHL) to a subject according to the test condition with random time interval which is set in step (a), tracing the wave V peak, and setting time sections which are both A and B sections containing wave V peak and SN10 peak respectively; (f) setting initial intensity of the test stimulus which is the minimal intensity where the potential difference between A and B section does not exceed the critical value fixed in advance in step (a); and (g) as a main test, presenting test stimulus of each frequency, searching the minimal intensity where the potential difference between A and B section does not exceed the critical value fixed in advance in step (a), and determining objective hearing threshold of each frequency.

The step (a) is for setting test condition. This step comprises the steps of: choosing the number of testing frequency; setting filtering frequency of notch filter to eliminate electrical background noise influxed from electrical source; setting frequencies of high-pass band filter and low-pass band filter to eliminate low-frequency artifact from brain and high-frequency electrical harmonics, respectively; setting the number of averaging; setting time range to randomize the time intervals between sequentially presented stimuli; setting both time range and critical intensity value of potential change, which is needed to classify an abrupt potential change during the test as an artifact and to exclude the epoch with the abrupt potential change from averaging process; setting a critical value which means a significant potential difference between section A containing positive peak of wave V and section B containing negative peak of SN10; and setting specifications for both coordinates and graphic images which are visualized in a user interface.

The step (b) is the same as the conventional method for converting subject's spontaneous EEG, which is influxed from electrodes placed on a subject's head before starting test, into a real-time graphic image.

The step (c) is a quantitative visualization of FFT analysis data on periodic artifacts among subject's spontaneous EEG. In this step, a large number of notch filters are needed to completely eliminate minute artifacts influxed from electrical harmonics, because the minute artifacts cannot be completely eliminated by a small number of notch filters, which are generally used for elimination of electrical harmonics. For accurate filtering of minute artifacts influxed from electrical harmonics, real-time frequency spectrum analysis for influxed potential is required, and it is desirable to use FFT analysis.

The step (d) is an arbitrary filtering by a user of distinctive periodic artifacts, which is based on the FFT analysis data of step (c). In this step, it is desirable to prudently use notch filters by considering the frequency and intensity of electrical harmonics, and the same frequency as that of the corresponding harmonics artifact is applied as the frequency of a notch filter.

The step (e) is a preliminary test. In this step, after searching the wave V peak, the A and B section, which comprises wave V peak and SN10 peak, respectively, is determined. In detail, the step (e) comprises the steps of: presenting standard test stimulus (e.g. 2 KHz, 90 dBHL, standard stimulus can be arbitrarily set by a user) to a subject according to the test condition with random time interval which is set in step (a); real-time counting and notifying the number of epochs included (accepted) for averaging and the number of epochs excluded (rejected) from averaging process according to the criteria of the epoch with the abrupt potential change fixed in step (a); averaging the accepted epochs where there seems to be no abrupt potential change; band-pass filtering of averaged data by applying the frequencies determined in step (a) to eliminate low-frequency artifact from brain and high-frequency electrical harmonics; notch filtering of stimulus artifact generated in concert with the presented stimulus, by applying the same frequency as that of the test stimulus; real-time imaging of the averaged EEG data on coordinates, according to the number of averaging and coordinates standard fixed in step (a); and after searching the positive peak of evoked wave V, setting time sections which are both A and B sections containing wave V positive peak and SN10 negative peak, respectively. An example of conditional sentences used to set the A and B section is as follows; "if the generation time of wave V peak, which is between 6 ms and 9 ms of averaged EEG section, is set to X, A section is (X−0.5)ms~(X+0.5) ms and B section is (X+1.5)ms~(X+3.5)ms."

The step (f) is setting initial intensity of the test stimulus for main test. By gradually decreasing stimulus intensity (e.g. 90, 85, 80, 75 dBHL or dBnHL) in the preliminary test, minimal intensity, at which the potential difference between A and B section does not exceed the critical value fixed in advance in step (a), is found out and set to Y. The initial stimulus intensity of a main test is set to Y+Z dB. (Z could be 5, 10, 15, 30, etc.)

Finally, the step (g) is a main test. After presenting test stimulus of each frequency to a subject and searching the minimal intensity of each frequency where the potential difference between A and B section does not exceed the critical value fixed in advance in step (a), the objective hearing threshold of each stimulus frequency is determined. Detail methods and processes applied to step (g) are the same as that of step (e).

BRIEF DESCRIPTION OF THE DRAWINGS

FIG. 1 is a configuration chart of a device for performing objective automated hearing test according to a preferred embodiment of the present invention.

FIG. 2 is a flow chart illustrating whole process of objective automated hearing test according to a preferred embodiment of the present invention.

MODE FOR THE INVENTION

Hereinafter, the preferred embodiment of the present invention will be described with reference to the accompanying drawings.

The present invention provides with a method and a device for automated tone-pip (or tone-burst) ABR test without both manual operation and user's subjective judgment, for determination of objective hearing thresholds based on the gap between wave V and SN10, and for acquisition of excellent signal-to-noise ratio by only minimal number of averaging.

The device for performing objective automated hearing test is firstly described and embodiments for performing automated tone-pip ABR test without both manual operation and user's subjective judgment, determination of objective hearing thresholds based on the gap between wave V and SN10, and obtaining excellent signal-to-noise ratio by only minimal number of averaging are described in this specification.

FIG. 1 is a configuration chart of a device for performing objective automated hearing test according to a preferred embodiment of the present invention.

Referring to FIG. 1, the part for both EEG analysis and hearing threshold determination is firstly illustrated 100.

If evoked EEG analysis data indicates that hearing threshold is not determined, next stimulus is presented 102.

Concerning the method of stimulus presentation, unpredictable stimulus to both a user and a subject is presented in the present invention. This is accomplished by random processing of stimulus presenting part and is totally different from the conventional method. Generally used frequencies of tone-pip (or tone-burst) stimuli for objective hearing test are as follows; 250 Hz, 500 Hz, 1000 Hz, 2000 Hz, and 8000 Hz. The number of tone-pip stimulus can be increased by applying subdivided frequency interval.

Wide range of stimulus intensity from maximum of 130 dBSPL to minimum can be used for the test.

Test stimulus is presented to a subject's ear not directly through a speaker but after passing trigger part 104. The trigger part transmits synchronization signal (114) of stimulus onset time to the EEG analysis part 100, which is needed to define initial time for averaging, and at the same time presents the stimulus to a subject through a speaker 106.

Concerning the location of electrodes placed to a subject, it is recommended to place an electrode on the upper part of subject's frontal lobe in the preferred embodiment of the present invention performing objective automated hearing test. The frontal lobe is a proper spot for minimizing difficulties accompanied by electrode placement. In addition, even when diverse methods suggested in the present invention for improving signal-to-noise ratio are applied to hearing test, evoked EEG with excellent signal-to-noise ratio can be drawn out from the frontal lobe without any deterioration.

EEG influxed from the subject's frontal lobe is transmitted to EEG sampling part 112 through electrode connecting part 110.

Both EEG data and synchronization signal of stimulus onset time, which are drawn out by EEG sampling part and inputted by trigger part, respectively, are simultaneously transmitted to EEG analysis & hearing threshold determination part 100. After real-time analyzing, the subject's final hearing threshold of each stimulus frequency is determined.

FIG. 2 is a flow chart illustrating whole process of objective automated hearing test according to a preferred embodiment of the present invention.

Referring to FIG. 2, in advance of performing objective automated hearing test, test condition is set 200.

Test condition setting comprises the steps of: choosing the number of testing frequency; setting filtering frequency of notch filter to eliminate electrical artifacts influxed from electrical source; setting frequencies of high-pass band filter and low-pass band filter to eliminate low-frequency artifact from brain and high-frequency electrical harmonics, respectively; setting the number of averaging; setting time range to randomize the time intervals between sequentially presented stimuli (i.e., inter-stimulus interval, ISI); setting both time range and critical intensity value of potential change, which is needed to classify an abrupt potential change during the test as an artifact and to exclude the epoch with the abrupt potential change from averaging process; setting a critical value which means a significant potential difference between section A containing positive peak of wave V and section B containing negative peak of SN10; and setting standards for both coordinates and graphic images which are visualized in a user interface.

After setting test condition, subject's spontaneous EEG, which is influxed from electrodes attached to the subject's head before testing, can be converted into a real-time graphic image. This step is the same as the conventional methods 202.

Next step 204 is a quantitative visualization of FFT analysis data on periodic artifacts among subject's spontaneous EEG. In this step, many number of notch filters are needed to completely eliminate minute artifacts influxed from electrical harmonics, because the minute artifacts cannot be completely eliminated by a small number of notch filters, which are generally used for elimination of electrical harmonics. For accurate filtering of minute artifacts influxed from electrical harmonics, real-time frequency spectrum analysis of influx potential is required, and it is desirable to use FFT analysis.

Based on the FFT analysis data, distinctive periodic artifacts are arbitrarily filtered by a user 206. In this step, it is desirable to use notch filters considering the frequency and intensity of electrical harmonics, and the same frequency as that of the corresponding harmonics artifact is applied as the frequency of a notch filter.

The accuracy and reliability of hearing test can be increased by a preliminary test followed by a main test. In this step, once a user presses the start button, standard test stimulus is presented 208. Though 2 KHz, 90 dBHL (or 60 dBnHL) tone-pip stimulus is usually used as a standard test stimulus, it can be arbitrarily set by a user. All the test stimulus containing standard test stimulus are presented to a subject with random time interval fixed in the step of test condition setting.

While standard test stimulus is presented to a subject, an abrupt potential change, which distorts the final data of averaging, can be generated together with evoked potential by tone-pip stimulus. During ensemble averaging process, it is desirable to completely eliminate the epochs, which are containing the abrupt potential change 210. The elimination of epochs is accomplished according to the criteria fixed in the step of test condition setting, which includes time section and critical intensity.

The epochs without abrupt potential change are averaged by the conventional method 212.

By band-pass filtering of averaged data, wave form is changed sharply or softly and low-frequency artifacts from brain and high-frequency electrical harmonics are eliminated 214.

As stimulus artifact, which is generated in concert with the presented stimulus, can be reflected to the final averaged data, notch filtering applying the same frequency as that of the test stimulus is included 216.

The peak of wave V is found out from the final averaged data 218.

After searching the wave V peak, both A and B sections, which contain the positive peak of wave V and negative peak of SN10 respectively, are set 220. An example of conditional sentences used to set the A and B sections is as follows; "if the generation time of wave V peak, which is between 6 ms and 9 ms of averaged EEG section, is set to X, A section is (X−0.5)ms~(X+0.5) ms and B section is (X+1.5)ms~(X+3.5) ms."

By gradually decreasing (e.g. 90, 85, 80, 75 dBHL) or increasing (e.g. 95, 100, 105 dBHL) stimulus intensity, the minimal intensity, at which the potential difference between A and B section does not exceed the previously fixed critical value, is found out and set to Y. The initial stimulus intensity of a main test is set to Y+Z dB 222.

In a main test 224~232, after presenting test stimulus of each frequency to a subject and searching the minimal intensity of each frequency where the potential difference between A and B section does not exceed the previously fixed critical value, the objective hearing threshold of each stimulus frequency is determined. Detail methods and processes applied to the main test are the same as that of a preliminary test except diversity of test stimulus frequency.

INDUSTRIAL APPLICABILITY

As described above, according to the preferred embodiment of the method and device for objective automated hearing test, users can shorten testing time by automatically performing tone-pip (or tone-burst) ABR test without both manual operation and user's subjective judgment. Further, according to the preferred embodiment of the present invention, in spite of minimization of the averaging number, reliable hearing test data with excellent signal-to-noise ratio is obtained by applying a decision method of objective hearing thresholds based on the gap between wave V and SN10.

The invention claimed is:

1. A method for performing an automated hearing test by using auditory brainstem response (ABR), the method comprising the steps of:
   providing a device configured to conduct EEG (electroencephalogram) analysis and determine a hearing threshold of a subject;
   presenting at least a test stimulus of each frequency of a plurality of testing frequencies to the subject's ear;
   using the device to set an A section including a Wave V peak and a B section including a SN10 peak based on a generation time of the Wave V peak using averaged potential data, wherein the B section follows the A section, and a potential difference is generated between the A and B sections; and
   using the device to search a minimal intensity where the potential difference between the A and B sections does not exceed a preset critical value, in order to determine the minimal intensity as the hearing threshold of each frequency.

2. The method of claim 1, further comprising:
   determining an initial intensity of the test stimulus of each frequency based on the minimal intensity where the potential difference between the A section and the B section does not exceed than a preset critical value prior to the step of searching the minimal intensity.

3. The method of claim 2, wherein by gradually decreasing or increasing an intensity of the test stimulus by 5 dBHL, the minimal intensity, at which the potential difference between the A section and the B section does not exceed the preset critical value is set to Y, and the initial intensity of the test stimulus is set to Y+ZdB in the step of determining the initial intensity.

4. The method of claim 1, further comprising:
   measuring the subject's spontaneous influx from electrodes placed on the subject's head;
   analyzing FFT data on periodic artifacts among the subject's spontaneous EEG; and
   filtering distinctive periodic artifacts based on the FFT analysis data.

5. The method of claim 4, wherein the subject's spontaneous EEG is converted into a real-time graphic image, and the FFT analysis data is visualized quantitative.

6. The method of claim 4, wherein the distinctive periodic artifacts are filtered by applying a corresponding the frequency of the periodic artifacts as a filtering frequency of a notch filter.

7. The method of claim 6, further comprising:
   choosing a number of the testing frequencies;
   setting the filtering frequency of the notch filter to eliminate electrical artifacts influxed from an electrical source;
   setting frequencies of a high-pass band filter and a low-pass band filter to eliminate low-frequency artifacts from brain and high-frequency electrical harmonics, respectively;
   setting a time range to randomize time intervals between sequentially presented stimuli;

setting both time range and critical intensity value of potential changes, in order to classify an abrupt potential change during the test as an artifact and to exclude an epoch with the abrupt potential change from an averaging process; and setting a critical value corresponding to a significant potential difference between the section A containing a positive peak of wave V and the section B containing a negative peak of SN10.

8. The method of claim 7, further comprising:

real-time counting the number of epochs included for averaging and the number of epochs excluded from averaging process according to a preset criteria of epoch;

averaging the epochs if no abrupt potential change between the A and B sections;

band-pass filtering of averaged data by applying a-preset frequencies to eliminate the low-frequency artifacts from brain and the high-frequency electrical harmonics; and notch filtering of a stimulus artifact generated in concert with the presented stimulus, by applying the same frequency as that of the test stimulus.

9. The method of claim 1, wherein the A section is set in the range of X−a to X+b ms, the B section is set in the range of X+b to X+c when generation time of the Wave V peak is set to X, and wherein each of a, b and c is a real number.

10. An apparatus for performing an automated hearing test by using auditory brainstem response (ABR), the apparatus comprising:

a stimulus presentation device that outputs at least a test stimulus of each frequency having a preset intensity in accordance with random time intervals;

an EEG (electroencephalogram) analysis device configured to set an A section including a Wave V peak and a B section including a SN10 peak based on a generation time of the Wave V peak using averaged potential (EEG) data, wherein the B section follows the A section, and a potential difference is generated between the A and B sections; and a hearing threshold determination device that is combined with the EEG analysis device, and which searches a minimal intensity where the potential difference between the A and B sections does not exceed a preset critical value, in order to determine the minimal intensity as a hearing threshold of a subject at each frequency.

* * * * *